(12) United States Patent
Miculka et al.

(10) Patent No.: US 6,689,884 B1
(45) Date of Patent: Feb. 10, 2004

(54) SUPRAMOLECULAR PAIRING SYSTEM, ITS PREPARATION AND USE

(75) Inventors: Christian Miculka, Frankfurt (DE); Norbert Windhab, Hattersheim (DE); Albert Eschenmoser, Küsnacht (CH); Stefan Scherer, Büttelborn (DE); Gerhard Quinkert, Glashütten (DE)

(73) Assignee: Nanogen Recognomics GmbH, Frankfurt (DE)

( * ) Notice: Subject to any disclaimer, the term of this patent is extended or adjusted under 35 U.S.C. 154(b) by 0 days.

(21) Appl. No.: 09/509,040

(22) PCT Filed: Sep. 21, 1998

(86) PCT No.: PCT/EP98/06002

§ 371 (c)(1),
(2), (4) Date: Aug. 3, 2000

(87) PCT Pub. No.: WO99/15509

PCT Pub. Date: Apr. 1, 1999

(30) Foreign Application Priority Data

Sep. 22, 1997 (DE) .......................... 197 41 739

(51) Int. Cl.[7] ...................... C07D 239/00; C07D 473/00
(52) U.S. Cl. ...................... 544/242; 544/264; 536/23.1; 536/27.1; 536/27.11
(58) Field of Search ................ 536/23.1, 27.1, 536/27.11; 544/242, 264

(56) References Cited

U.S. PATENT DOCUMENTS 5,382,580 A   1/1995   Chen et al.

FOREIGN PATENT DOCUMENTS

| EP | 468352 A2 | 1/1992 |
|---|---|---|
| WO | WO 93/13121 A1 * | 7/1993 |
| WO | WO 97/43232 A1 * | 11/1997 |
| WO | WO 98/25943 A1 * | 6/1998 |
| WO | WO 99/15509 A2 * | 4/1999 |

OTHER PUBLICATIONS

Schaeffer et al., "Enzyme Inhibitors. XIX. The Synthesis of Some 1–Hydroxy–2–hydroxymethyl–4–(6–substituted–9–purinyl)cyclohexanes as Nucleoside Analogs," *Journal of Medicinal Chemistry*, 11(1), 15–20 (Jan., 1968).††.*

Pérez–Pérez et al., "Application of the Mitsunobu–Type Condensation Reaction to the Synthesis of Phosphonate Derivatives of Cyclohexenyl and Cyclohexanyl Nucleosides," *Journal of Organic Chemistry*, 60(6), 1531–1537 (Jun., 1995).††.*

Mikhailov et al., "Use of Cyclohexene Epoxides in the Preparation of Carbocyclic Nucleosides," *Nucleosides & Nucleotides*, 15(4), 867–878 (1996).††.*

Marquez et al., "Carbocyclic Nucleosides," *Medicinal Research Reviews*, 6(1), 1–40 (Jan. 1, 1986).††.*

Borthwick et al., "Synthesis of Chiral Carbocyclic Nucleosides," *Tetrahedron*, 48(4), 571–623 (Jan. 24, 1992).††.*

Knapp, "Iodolactamization: Aspects and Applications," *Advances in Heterocyclic Natural Product Synthesis*, vol. 3, JAI Press, Inc., 1996, only pp. 57–98 suppied.††.*

Crane et al., "Isonucleosides from Glucosamine," *Journal of Carbohydrates • Nucleosides • Nucleotides*, 7(5), 281–296 (1980).*

Knapp, Spencer et al. "Iodolactamization: 8–exo–iodo–2–azabicyclo[3.3.0]octan–3–one." Organic Syntheses 70: 101–10 (1992).

Verheggen, I., et al. "Synthesis and Antiherpes Virus Activity of 1,5–Anhydrihexitol Nucleosides." J. Med. Chem. 26: 2033–40 (1993). (Issue No. 14).

* cited by examiner

Primary Examiner—James O. Wilson
Assistant Examiner—Lawrence E Crane
(74) Attorney, Agent, or Firm—O'Melveny & Myers LLP

(57) ABSTRACT

The invention relates to a compound of formula (I), wherein $R^1$ is $NR^3R^4$, $OR^3$ or $SR^3$ with $R^3$ and $R^4$ being H or $C_nH_{2n+1}$ independently of each other and being the same or different, n being a whole number from 1 to 12; $R^2$ is equal to $C_mH_{2m}$—C(X)—Y with X being =O, =S or =N, Y being equal to $OR^3$, $NR^3R^4$ or $SR^3$, $R^3$ and $R^4$ having the same meaning given above, and m being a whole number from 1 to 4; or $R^2$ is equal to $C_mH_{2m}$—Z—Y' with Z being a sulfonyl, phosphonyl, ether or amine group, Y' being equal to H, $C_nH_{2n+1}$, $OR^3$, $NR^3R^4$ or $SR^3$ then Z is sulphonyl or phosphonyl group, n, $R^3$ and $R^4$ having the meaning given above, and Y' being equal to $C_nH_{2n+1}$ when Z is an ether or an amine group; A, B, and D are the same or different and mean $CR^5R^6$, O, $NR^7$ ou S independently of each other with $R^5$, $R^6$ and $R^7$ being H or $C_nH_{2n+1}$, independently of each other, n having the meaning given above; and C is equal to $CR^8$ or N with $R^8$ having the meaning of $R^5$ independently, A—B, B—C or C—D not being two identical heteroatoms; and nucleobase means thymine, uracile, adenine, cytosine, guanine, isocytosine, isoguanine, xanthine or hypoxanthine. The invention also relates to a method for producing these derivatives and to their use in pairing and/or testing systems.

(I)

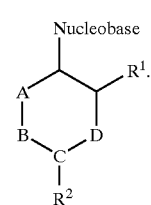

16 Claims, 5 Drawing Sheets

SEQUENCE LISTING

<160> NUMBER OF SEQ ID NOS: 2

<210> SEQ ID NO 1
<211> LENGTH: 6
<212> TYPE: PRT
<213> ORGANISM: Homo sapiens

<400> SEQUENCE: 1

Cys Tyr Ser Lys Val Gly
1               5

<210> SEQ ID NO 2
<211> LENGTH: 5
<212> TYPE: PRT
<213> ORGANISM: Homo sapiens

<400> SEQUENCE: 2

Cys Ser Lys Val Gly
1               5

SUPRAMOLECULAR PAIRING SYSTEM, ITS PREPARATION AND USE

The present invention relates to a compound of the formula I

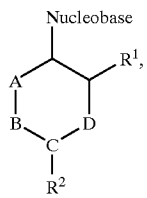

its preparation and use in pairing and/or test systems.

Pairing systems are supramolecular systems of non-covalent interaction, which are distinguished by selectivity, stability and reversibility, and their properties are preferably influenced thermodynamically, i.e. by temperature, pH and concentration. DNA and RNA play a fundamental role here as carriers of the genetic traits. Such pairing systems can be used, for example, as a result of their selective properties but also as "molecular adhesive" for the bringing together of different metal clusters to give cluster associations having potentially novel properties [R. L. Letsinger, et al., Nature, 1996, 382, 607–9; P. G. Schultz et al., Nature, 1996, 382, 609–11).

Strong and thermodynamically controllable pairing systems therefore play a more and more important role for use in the field of nanotechnology, for the preparation of novel materials, diagnostics, therapeutics and microelectronic, photonic and optoelectronic components and for the controlled bringing together of molecular species to give supramolecular units, such as, for example, the (combinatorial) synthesis of protein assemblies [see, for example, A. Lombardi, J. W. Bryson, W. F. DeGrado, Biomoleküls (Pept. Sci.) 1997, 40, 495–504].

For the preparation of pairing systems of this type, DNA and RNA units, however, have the following disadvantages:
a) The forces which hold together the two strands, especially hydrogen bridges and stacking effects, are naturally very low. Such duplices therefore have a low stability. This can be easily determined by recording of a so-called transition curve and determination of the transition point. Consequently, for the preparation of pairing systems relatively long individual strands are necessary, which has the result that the portion of the pairing system on the supramolecular unit predominates, i.e. the "nucleotide load" is high.
b) Owing to the formation of Hoogsteen pairings, which are possible alternatively to Watson-Crick pairings, the selectivity decreases. Parallel duplices or irreversible pairing processes are thus often combined.
c) Owing to the high flexibility of the sugar phosphate backbone, helical conformations are formed, as a result of which the spatial arrangement in supramolecular units can be less readily controlled.
d) The chemical instability of the phosphodiester bond in the backbone permits only a slight variance in physical conditions, such as pH or temperature, for the use of the supramolecular units.
e) The nuclease sensitivity of the products leads to a rapid enzymatic degradation, which can only be avoided with difficulty, and thus to the destruction of the supramolecular unit.
f) Possible interference with the genetic material of biological systems is not to be excluded if the supramolecular units are used in a biological system, i.e. an orthogonality of the pairing process is absent.
g) The preparation of relatively large amounts of oligonucleotides is difficult on account of the low loading ability of the solid phase customarily used, for example in comparison with peptide synthesis.
h) The preparation of the unnatural L enantiomeric form is made difficult by the poor accessibility of the appropriately configured sugar units.

Thus use of DNA or RNA units, for example, in complementarily bonded two- and three-dimensional supramolecular structures (see, for example, WO96/13522) in a physiological medium can only be realized with difficulty, especially in view of item e), f) and g).

An alternative to DNA and RNA units is the so-called pyranosyl-RNA (p-RNA). pRNA is an oligonucleotide which contains ribopyranose as a sugar unit instead of ribofuranose and therefore exclusively forms Watson-Crick-paired, antiparallel, reversibly "melting", quasi-linear and stable duplices. In addition, there are also homochiral p-RNA strands with an opposite sense of chirality, which likewise pair controllably and are not strictly helical in the duplex formed. This valuable specificity for the synthesis of supramolecular units is connected with the relatively low flexibility of the ribopyranose phosphate backbone and with the strong inclination of the base plane to the strand axis and the tendency resulting from this for intercatenary base stacking in the resulting duplex and can finally be attributed to the participation of a 2',4'-cis-disubstituted ribopyranose ring in the synthesis of the backbone. p-RNA thus solves some of the described disadvantages of DNA and RNA, but not the disadvantages according to items d), e), g) and h).

A further alternative is the linkage of the monomer units by means of amide bonds, i.e. the synthesis of an oligomeric peptide, so-called peptide nucleic acids (PNAs).

Owing to their open-chain structure, PNAs have a high flexibility and are thus not suitable for the controlled synthesis of supramolecular systems in view of their conformational preorganization.

It is therefore the object of the present invention to make available compounds which do not have the disadvantages described above.

One subject of the present invention is therefore compounds of the formula I

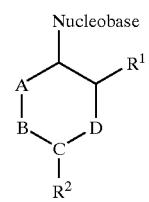

in which $R^1$ is equal to $NR^3R^4$, $OR^3$ or $SR^3$ where $R^3$ and $R^4$ independently of one another, identically or differently, are H or $C_nH_{2n+1}$, n being an integer from 1–12, preferably 1–8, in particular 1–4; preferably $R^1$ is equal to $NR^3R^4$ or $OR^3$, in particular $NR^3R^4$, especially $NH_2$;

$R^2$ is equal to $C_mH_{2m}$—C(X)—Y where X is equal to =O, =S or =N—H, wherein Y is $OR^3$, $NR^3R^4$ or $SR^3$, or $R^2$ is equal to $C_mH_{2m}$—$CH_2$—X or $C_mH_{2m}$—CH(X)—Y, wherein X is equal to $NR^3R^4$, $OR^3$, or $SR^3$; or $R^2$ is equal to $C_mH_{2m}$—Z—Y' where Z is equal to a $S(=O)_2$ or $P(=O)(O^-)$, wherein Y' is equal to H, $C_nH_{2n+1}$, $OR^3$, $NR^3R^4$ or $SR^3$, and wherein m is an integer from 1–4;

A, B and D independently of one another, identically or differently, are $CR^5R^6$, O, $NR^7$ or S where $R^5$, $R^6$, $R^7$ independently of one another are H or $C_nH_{2n+1}$, where n has the abovementioned meaning; and C is equal to $CR^8$ or N, where $R^8$ independently thereof denotes the meaning of $R^5$, but where A—B, B—C or C—D are not two identical heteroatoms; and the term nucleobase within the meaning of the present invention denotes thymine, uracil, adenine, cytosine, guanine, isocytosine, isoguanine, xanthine or hypoxanthine, preferably thymine, uracil, adenine, cytosine or guanine.

In particular, compounds are preferred in which $R^1$ is equal to $NH_2$ and $R^2$ is equal to $CH_2$—COOH, especially a [2-amino-4-(carboxymethyl)cyclohexyl]nucleobase, such as 1-[2-amino-4-(carboxymethyl)cyclohexyl]thymine, 1-[2-amino-4-(carboxymethyl)cyclohexyl]uracil, 1-[2-amino-4-(carboxymethyl)cyclohexyl]-cytosine, 9-[2-amino-4-(carboxymethyl)cyclohexyl]adenine or 9-[2-amino-4-(carboxymethyl)cyclohexyl]guanine.

It is furthermore advantageous if the compound according to the invention is enantiomerically pure.

For the synthesis, it is further advantageous if $R^1$ is also provided with protective groups, such as, for example, in the case of $R^1$ is equal to $NH_2$ with tert-butoxycarbonyl groups (BOC) or 9-fluorenylmethoxycarbonyl groups (FMOC) or in the case of $R^1$ equal to OH, with ether or acetal protective groups. Protective groups are in general understood as meaning radicals which protect reactive groups of compounds from undesired reactions and are easily removable. Groups of this type are, for example, benzyloxymethyl (BOM), BOC, FMOC, ether or acetal protective groups.

In addition, Y can also be reacted with activating reagents to give reactive intermediates, e.g. mixed anhydrides.

Preferably, the compounds according to the invention are cyclohexane derivatives which, in the 1'-position, carry a nucleobase and in the 2'-position a nucleophile, such as, for example, a nitrogen atom which can be reacted with the reactive group in the 4'-position or after its activation, such as, for example, with a carbonyl function, and thus by repetition of this process is able to build up an oligomeric structure. From the stereochemical point of view, derivatives are preferred in which all substituents on the 6-membered ring have equatorial positions, in particular in which the substituents in the 1'- and 2'-position have equatorial positions and especially in which the nucleobase has an equatorial position.

The compounds according to the invention can be prepared, for example, in the following way.

In the beginning, a chirogenic Diels-Alder reaction is carried out (see FIG. 1) between, for example, 1,3-butadiene 1 and, for example, 3-(2-propenoyl)-1,3-oxazolidin-2-one 2 in the presence of chiral, non-racemic promoters such as the Seebach's TADDOL 3 (D. Seebach et al., J. Org. Chem. 1995, 60, 1788). 3-(2-Propenoyl)-1,3-oxazolidin-2-one can be prepared, for example, by reaction of oxazolidin-2-one with acryloyl chloride in the presence of copper and copper (I) chloride. The compound 5 can be prepared, for example, from 4 in the presence of magnesium turnings and anhydrous methanol. The reaction product is then reduced, for example, with lithium aluminium hydride in order to give the compound 6. The acetonitrile 7 can be prepared from 6, for example, by reacting with methanoyl chloride to give methyl methanoate and then by reacting with cyanide. Alkaline hydrolysis of the reaction product forms the acetic acid derivative, which can be reacted with $SOCl_2$ to give the acetyl chloride to afford the acetamide 8 in the presence of an aqueous ammonia solution. Iodolactamization thereof is then carried out (S. Knapp et al., Org. Synth. 1991, 70, 101) to give the iodolactam 9.

The iodolactam 9 can then be coupled to a nucleobase in the presence of a hydride without the bicyclic system being destroyed.

For this, it is advantageous if possibly reactive groups of the nucleobase are protected by suitable protective groups, e.g. BOC, FMOC, acetal etc. Only in the case of diaminopurine as a nucleobase are protective groups unnecessary. However, it has been shown that in the case of diaminopurine as a nucleobase it was no longer possible to open the lactam ring. Independently of this, diaminopurine plays no role in biological systems.

It is furthermore preferred if the iodolactam is not present in racemic form, but in enantiomerically pure form, as the oligomers to be synthesized, which are intended to be a pairing system, should belong only to one stereochemical series. The synthesis of a pairing system from racemic units is in general not possible.

According to the present invention, a couplable pyrimidine unit, e.g. a thymine unit, can be prepared starting from the iodolactam 9 in a five-stage synthesis sequence in a yield of 27% over all steps (FIG. 2.):

In the first step, the stereoselective introduction of the nucleobase is carried out in a substitution reaction (13a) followed by the masking of the acidic imide proton of the thymine (13b). The lactam is then activated by introducing a protective group, e.g. the Boc group (13c), and the ring is opened nucleophilically, for example, by means of LiOOH (14a). After removing the BOM protective group which, for example, is present, the desired unit (14b) results by means of catalytic hydrogenation.

The enantiomorphic (R) unit ent-14b is obtainable by an analogous procedure from the (R)-iodolactam ent-9. Likewise, couplable uracil, cytosine and isocytosine units are obtainable analogously.

A couplable purine unit, e.g. an adenine unit, is accessible starting from the iodolactam 9 in a seven-stage synthesis sequence in a yield of 19% over all steps (FIG. 3.):

After introduction of the, for example, N(6)-benzoylated adenine into the (S)-iodolactam 9 with retention (15a) the reprotection to give the, for example, N(6)-formamidineadenine lactam 15c is carried out. The activation of the lactam, for example, by means of tert-butoxycarbonylation (15d), a new reprotection to give the, for example, N(6)-anisoyl-protected lactam (15f) and subsequent lactam cleavage, for example, by means of LiOH yields the desired unit 16 are then carried out.

The enantiomorphic (R) unit ent-16 is obtainable by an analogous procedure from the (R)-iodolactam ent-9. Likewise, couplable guanine, isoguanine, xanthine, and hypoxanthine units are obtainable analogously.

The preparation of heteroatom-containing six-membered rings and other derivatives of the compound according to the invention are [sic] possible, for example, analogously by means of a hetero-Diels-Alder reaction or by means of Diels-Alder reactions with the appropriate starting compounds.

Another subject of the present invention is therefore a process for the preparation of a compound according to the invention having the following steps:

(a) coupling of the appropriate iodocycloalkane, e.g. of an iodolactam, preferably of an enantiomerically pure iodocycloalkane, with a protected nucleobase preferably in the presence of a hydride, such as, for example, NaH, and in the case of an iodolactam (b) activation of the lactam, for example by introducing a protective group such as, for example, a BOC group, and (c) nucleophilic ring-opening, e.g. by means of a hydroperoxide such as, for example, LiOOH.

For the preparation of oligomers, the compounds according to the invention are then preferably synthesized on a solid phase according to the Merrifield peptide synthesis to give oligomeric structures. In this process, the necessary reagents are preferably added in an excess and unreacted amounts are removed again by simple washing steps [R. B. Merrifield, *J. Amer. Chem. Soc.* 1963, 85, 2149]. Repetitive cycles which consist of removals of the temporary protective groups and couplings, e.g. according to the symmetrical anhydride method, of the protected monomer units lead to the oligomers on the resin. At the end of the synthesis, the terminal protective group is removed, and the oligomer is cleaved from the resin and preferably purified using chromatographic methods. The isolated HPLC fractions of the synthesis products were checked for their purity using analytical HPLC and clearly characterized using electrospray mass spectrometry.

A further subject of the present invention is therefore an oligomer, called CAN (cyclohexylnucleooligoamide), comprising at least one compound according to the invention, which in general are [sic] linked 2'→4'.

In order to bring together molecular species, such as peptides, proteins, receptors, redox centres, antibodies, nucleic acid sections (such as DNA, RNA) with the aid of the pairing system described, in general suitable linkers are integrated. Preferably, but not exclusively, lysine can be incorporated at any desired position in the oligomeric pairing system, but very preferably terminally. Owing to its free amino group, lysine has a large number of linkage possibilities. Incorporation into the oligomer according to the invention is carried out, for example, by means of Boc-Lysine(Fmoc), whose FMOC group can be removed using piperidine in DMF.

The present invention therefore also relates to oligomers which additionally contain at least one linker, preferably a lysine linker, especially a terminal lysine linker.

The, for example, amino-functionalized oligomer can also preferably be derivatized with activated linkers such as, for example, iodoacetylsuccinimide (A) or bis(hydroxysuccinimidyl)glutarate (B), which then preferably react in physiological media, in particular in aqueous-buffered solutions optionally with addition of organic solubilizers, with HS groups of the molecular species, e.g. via (A) with the cysteine radicals of a peptide or protein or via (B) with amino groups of the molecular species with formation of chemically stable, covalent forms.

The present invention therefore also includes oligomers which are derivatized with an activated linker, such as, for example, iodoacetylsuccinimide and/or bis(hydroxysuccinimidyl)glutarate.

The oligomers according to the invention having a free N and C terminus are generally only poorly soluble in water at pH 7. In the case of tetramers, concentrations in the 100 $\mu$molar, in the case of pentamers in the 10 $\mu$molar and in the case of hexamers only approximately in the 1 $\mu$molar range, are achieved. These are approximate values which, depending on the sequence, can also be exceeded or fallen short of by an order of magnitude. The solubility of AAATT is, for example, 1 $\mu$M, that for AATAT 50 $\mu$M.

By acylation of the N terminus with a hydroxycarboxylic acid derivative, it is possible, for example, to introduce a hydroxyl function which can be phosphorylated. The phosphated oligomer thus obtained customarily is at least about 1000 times more soluble in water at about pH 7. The solubility is generally detected by UV spectroscopy. The present invention therefore also relates to phosphated oligomers.

Another subject of the invention is also a conjugate of an oligomer according to the invention and a biomolecule.

Biomolecule is understood according to the present invention as meaning, for example, a peptide, peptoid or protein, such as, for example, a receptor, an antibody or functional parts thereof or an enzyme, and a nucleic acid such as DNA or RNA, or cell constituents such as lipids, glycoproteins, filament constituents, or viruses, virus constituents such as capsids, viroids, and their derivatives such as, for example, acetates.

Functional parts of antibodies are, for example, Fv fragment (Skerra & Plückthun (1988) Science 240, 1038), single-chain Fv fragments (scFv; Bird et al (1988), Science 242, 423; Huston et al. (1988) Proc. Natl. Acad. Sci. U.S.A., 85, 5879) or Fab fragments (Better et al. (1988) Science 240, 1041). The conjugates according to the invention of effector molecules and preferably peptide, but in contrast to PNA, selective and controllable pairing systems are advantageous if reversibly supramolecular assemblies are to be synthesized, whose action, such as, for example, binding, inhibition, induction of a physiological effect, differs from the action of the individual effector molecules.

Thus, for example, WO 96/13613 describes a method for finding a substance which induces a biological action due to the multimerization of proteins by first determining a substance I which binds to a protein by means of a test, then determining a second substance II which binds to a second protein and then covalently linking the two substances I and II by means of a linker such that a dimerization of the two proteins is induced. This dimerization then brings about the desired biological effect. Such a method can achieve greater flexibility if the linkage of the two substances I and II takes place non-covalently, but by a pairing system such as the oligomer or conjugate according to the invention. Owing to the controllability of this pairing, for example by temperature or pH, the dimerization process of the proteins can be observed or its extent controlled. The pairing systems according to the invention have the advantage, for example compared with the systems from WO 96/13522, that they are nuclease-stable.

An attempt to use peptide "adhesive" units for the formation of homo- or heterodimeric assemblies is described, for example, in WO 94/28173:

Association peptides (hexa- or heptapeptides) of a fixed sequence bring together effector units, such as, for example, proteins, to give supramolecular units. Such a method can achieve higher flexibility due to controllability of this association process, which in general cannot be realized with the association peptides, but advantageously with the pairing systems of the present invention.

The invention therefore also relates to the use of the compound according to the invention, the oligomer according to the invention or the conjugate according to the invention in a pairing and/or test system, such as, for example, described in greater detail in WO 94/28173, WO 96/13522, WO 96/13613, R. L. Letsinger, et al., Nature, 1996, 382, 607–9; P. G. Schultz et al., Nature, 1996, 382, 609–11 or A. Lombardi, J. W. Bryson, W. F. DeGrado, Biomoleküls (Pept. Sci.) 1997, 40, 495–504 and generally explained above.

A particular embodiment of the present invention is a carrier on which a compound according to the invention, an oligomer according to the invention and/or a conjugate according to the invention is immobilized, in particular for use in a pairing and/or test system, as described in greater detail above.

The term "immobilized" is understood within the meaning of the present invention as meaning the formation of a covalent bond, quasi-covalent bond or supramolecular bond by association of two or more molecular species such as molecules of linear constitution, in particular peptides, peptoids, proteins, linear oligo- or polysaccharides, nucleic acids and their analogues, or monomers such as heterocycles, in particular nitrogen heterocycles, or molecules of non-linear constitution such as branched oligo- or polysaccharides or antibodies and their functional moieties such as Fv fragments, single-chain Fv fragments (scFv) or Fab fragments.

Suitable carrier materials are, for example, ceramic, metal, in particular noble metal, glasses, plastics, crystalline materials or thin layers of the carrier, in particular of the materials mentioned, or (bio)molecular filaments such as cellulose, structural proteins.

In summary, the present invention has the following advantages compared with conventional pairing and test systems:

The duplices of the oligomers or conjugates according to the invention are significantly more stable than those of DNA, RNA and p-RNA. The oligomeric substances are significantly more stable chemically and against enzymatic degradation, do not pair with DNA or RNA and can be prepared in relatively large amounts in a simple manner. Both enantiomers are easily accessible by synthetic chirogenic steps. The compounds according to the invention are therefore superior to the pairing systems known hitherto as selective "molecular adhesives".

The following figures and examples are intended to describe the invention in greater detail without restricting it.

EXAMPLES

Figure 1:
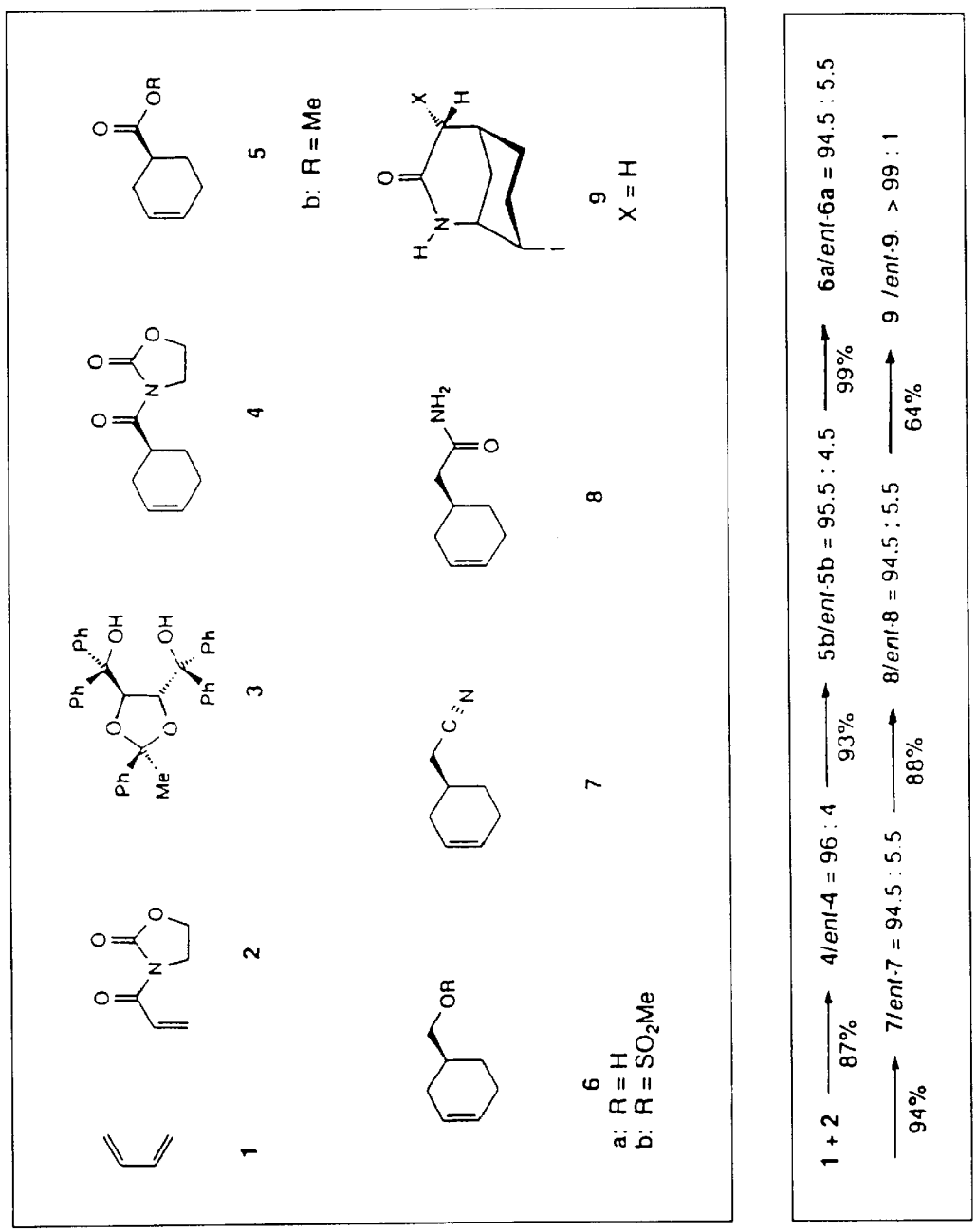
FIG. 1A shows schematically the synthesis of the iodolactam 9.
FIG. 1B shows schematically the synthesis of a couplable thymine unit.
FIG. 1C shows schematically the synthesis of a couplable adenine unit.
Figure 2:
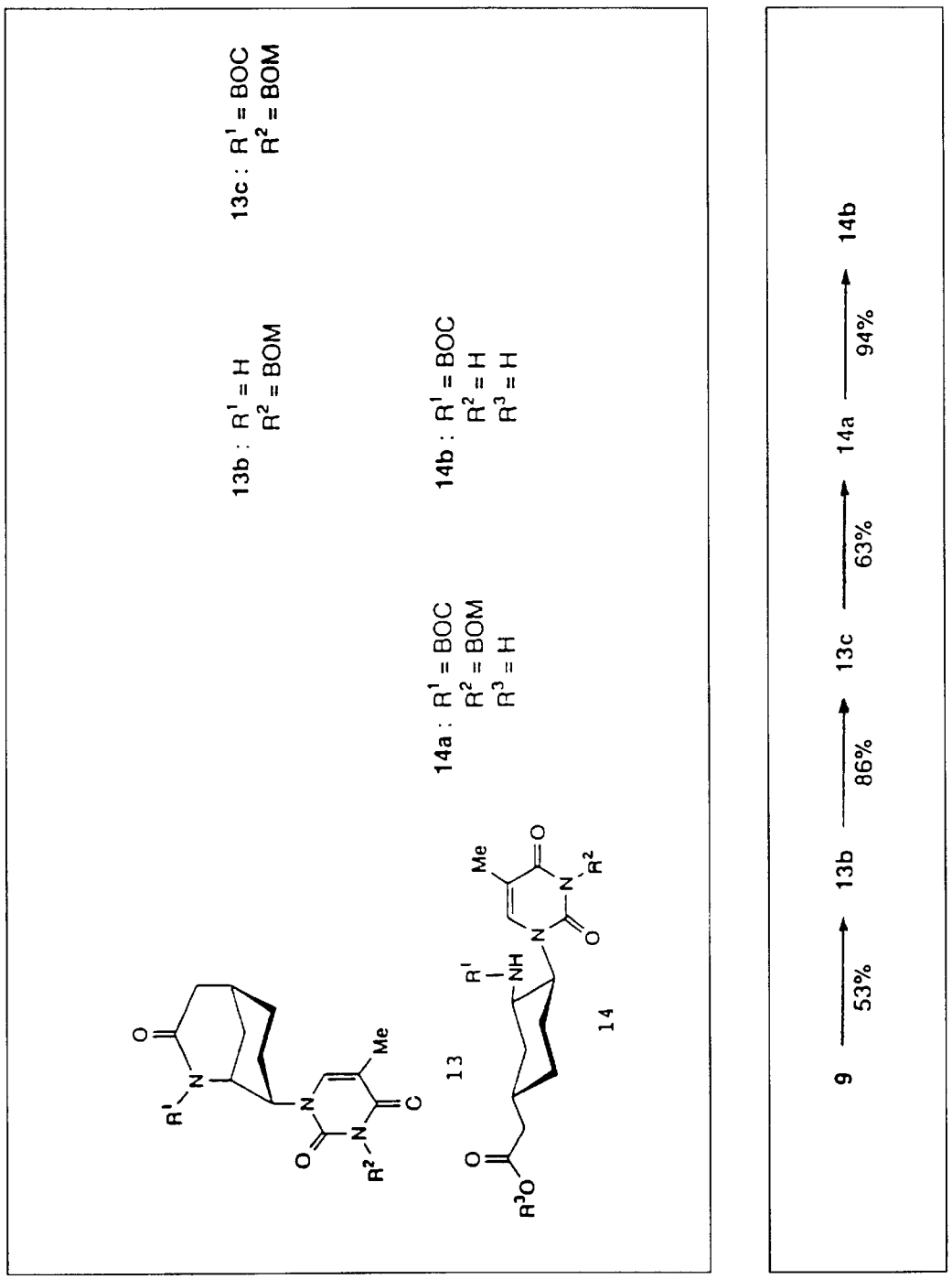
FIG. 2 shows the illustration of a reversible UV transition curve of the oligomer ATATA.
Figure 3:
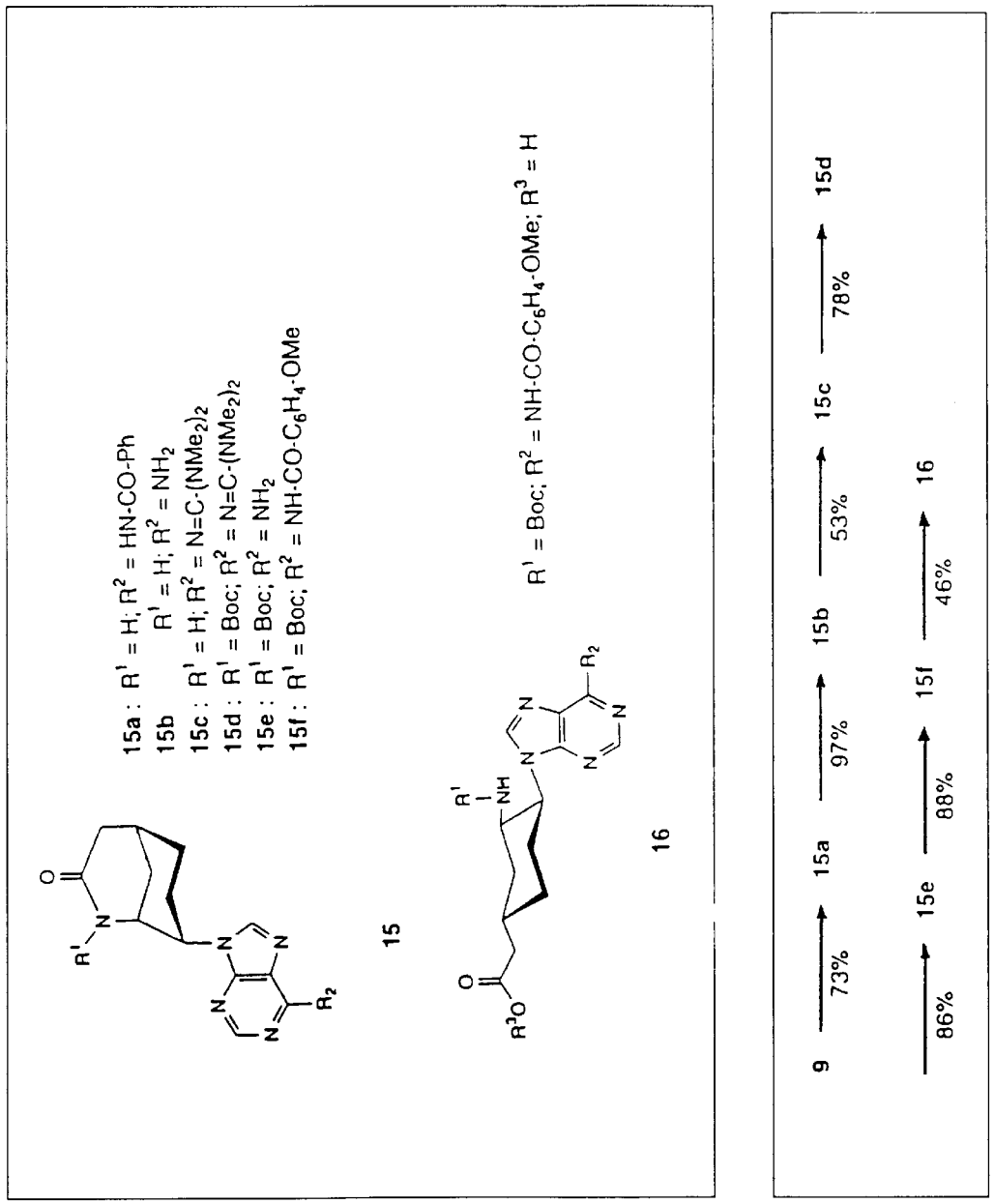
FIG. 3 shows the transition curve of phosphated Hba-AATAT.

Example 1
Synthesis of a Couplable Thymine Unit

Preparation of 1-[(S,S,S)-8-Azabicyclo[3.3.1]nonan-7-on-2-yl]-3-[(benzyloxy)methyl]thymine (13b)

1. Procedure 148 mg (4.00 mmol) of a 65% strength NaH suspension were introduced into a dry 50 ml Löwenthal flask flushed with protective gas, washed twice with 5 ml each of anhydrous pentane and suspended in 20 ml of DMF. 493 mg (2.00 mmol) of 3-(benzyloxy)methylthymine were first added in portions and, after the evolution of gas had subsided, 530 mg (2.00 mmol) of 9 were added. After stirring at room temp. for about 20 minutes, a pale yellow reaction solution was formed, which was stirred overnight at room temp.

The reaction solution was treated with 1 ml of a satd aqueous $NH_4Cl$ solution and transferred into a round-bottomed flask with rerinsing with MeOH. Subsequently, the solvents were first cautiously removed in vacuo in a rotary evaporator, then by bulb-tube distillation (70° C./0.5 torr). 1.71 g of a yellow-orange-coloured oil were obtained, which was purified by MPL chromatography on 150 g of silica gel 60 ($CH_2Cl_2$/MeOH 30:1). The solid thus obtained was digested with a little $Et_2O$, filtered off, comminuted and dried in an oil pump vacuum. This yielded 405 mg (53%) of 13b (ent-13b: 50%; rac-13: 51%) as a colourless powder m.p. 160–162° C. An analytical sample was obtained by crystallization from THF/cyclohexane.

2. Analytical Data

1-[(S,S,S)-8-Azabicyclo[3.3.1]nonan-7-on-2-yl]-3-[(benzyloxy)methyl]thymine (13b):

M.p.: 160–162° C. (THF/cyclohexane); ent-13b: 161–162° C. rac-13b: 186–188° C. (THF/cyclohexane). TLC: $CH_2Cl_2$/MeOH 15:1, $R_f$ 0.41. Spec. rotation: $[\alpha]_{589}^{20}$=–43.3° (c=1.10, $CH_2Cl_2$); ent-13b: $[\alpha]_{589}^{20}$=+42.9° (c=1.05, $CH_2Cl_2$). UV ($CH_3CN$): $\lambda_{max}$ 274.2 (9623). IR (KBr): 3447w, 3189w, 3090w, 2949m, 2906m, 1703s, 1652s, 1464s, 1405s, 1357s, 1270s, 1076s. $^1$H-NMR (300 MHz, $d_6$-DMSO): 1.59 ($m_c$, 3H, H—C(4'), 2H—C(9')); 1.85 ($m_c$, H—C(3')); 1.88 (s, $CH_3$); 2.00–2.14 (m, 3H, H'—C(3'), H'—C(4'), H—C(6')); 2.20 (br. s, H—C(5')); 2.47 (dd, J(H'—C(6'), H—C(6'))=18.5, J(H'—C(6'), H—C(5'))=7.5, H'—C(6')); 3.58 (br. m, H—C(1')); 4.22 (br. m, H—C(2')); 4.60 (s, 2H, PhCH$_2$O); 5.35 ($m_c$, 2H, OCH$_2$N); 7.22–7.35 (m, 5H, Ph); 7.54 (s m. Fs., H—C(6)); 7.99 (d, J(H—N(8'), H—C(1'))=4.6, H—N(8')).

The assignment of the signals was carried out with the aid of a $^1$H, $^1$H-COSY spectrum.

$^{13}$C-NMR (75 MHz, $d_6$-DMSO): 12.75 ($CH_3$); 17.90 (C(3')); 23.82 (C(9')); 24.66 (C(5')); 27.47 (C(4')); 37.15 (C(6')); 47.27 (C(1')); 55.55 (C(2')); 70.45 (OCH$_2$N); 71.06 (PhCH$_2$O); 107.82 (C(5)); 127.06, 127.29, 128.03 (5C, Ph); 137.40 (C(6)); 138.18 ($C_{ipso}$); 151.04 (C(2)); 162.67 (C(4)); 170.83 (C(7')).

The assignment of the signals was carried out with the aid of a $^1$H, $^{13}$C-COSY spectrum.

MS (ESI$^+$): 767.8 [2M+H], 384.5 [M+H]. Anal.: calc. for $C_{21}H_{25}N_3O_4$ (383.45): C, 65.78, H, 6.57, N, 10.96; found: C, 65.68, H, 6.64, N, 10.84.

Preparation of 1-[(S,S,S)-8-aza-8-(tert-Butoxycarbonyl)bicyclo[3.3.1]nonan-7-on-2-yl)-3-[(benzyloxy)methyl]thymine (13c)

1. Procedure 7.18 g (18.7 mmol) of 13b were dissolved in a 250 l round-bottomed flask and treated successively with 2.59 ml (18.7 mmol, 1 eq.) of NEt$_3$ and 8.00 ml (37.4 mmol, 2 eq.) of Boc$_2$O. Subsequently, 2.28 g (18.7 mmol, 1 eq.) of DMAP were added by spatula and the yellow reaction solution was stirred at room temp. for 4 hours. 3.89 ml (28.1 mmol, 1.5 eq.) of NEt$_3$, 12.0 ml (56.1 mmol, 3 eq.) of Boc$_2$O and 3.43 g (28.1 mmol, 1.5 eq.) of DMAP were again added successively. After stirring overnight with exclusion of water, traces of starting material were still present according to TLC checking (silica gel 60; $CH_2Cl_2$/MeOH 15:1). 2.00 ml (9.35 mmol) each of Boc$_2$O were therefore again added at an interval of four hours. The mixture was again stirred overnight with exclusion of water and the solvents and reagents were subsequently removed in vacuo in a rotary evaporator. This yielded 19.5 g of an oily, yellow solid, which was chromatographed on 275 g of silica gel 60 (AcOEt/n-heptane 2:1). 8.50 g of a slightly yellow-coloured solid were obtained. Recrystallization from 50 ml of THF and 100 ml of cyclohexane yielded 7.81 g (86%) of 13c (ent-13c: 87%; rac-13c: 85%) as colourless, small crystals of m.p. 124–126° C.

2. Analytical Data

1-[(S,S,S)-8-aza-8-(tert-Butoxycarbonyl)bicyclo[3.3.1] nonan-7-on-2-yl]-3-[(benzyloxy)methyl]thymine (18):

M.p.: 124–126° C. (THF/cyclohexane); ent-13c: 123–125° C. rac-13c: 125–127° C. (THF/cyclohexane). TLC: AcOEt/n-heptane 2:1, $R_f$ 0.13. Spec. rotation: $[α]_{589}^{20}$=–10.3° (c=1.37, $CH_2Cl_2$); ent-13c: $[α]_{589}^{20}$=+ 10.6° (c=1.20, $CH_2Cl_2$). UV ($CH_3CN$): $λ_{max}$ 273.6 (10200). IR (KBr): 3447w, 2934w, 1744s, 1701m, 1663s, 1448m, 1363m, 1260s, 1153m, 1078m. $^1$H-NMR (300 MHz, $CDCl_3$): 1.49 (s, 9H, C(CH$_3$)$_3$); 1.52–1.63, 1.74–2.13 (2m, 6H, 2H—C(3'), 2H—C(4'), 2H—C(9')); 1.88 (s, CH$_3$—C (5)); 2.33 (br. s, H—C(5')); 2.38 (d, J(H—C(6'), H'—C(6'))= 18.2, H—C(6')); 2.70 (dd, J(H'—C(6'), H—C(6'))=18.2, J(H'—C(6'), H—C(5'))=6.7, H'—C(6')); 4.27 ($m_c$, H—C (1')); 4.40 ($m_c$, H—C(2')); 4.65 (s, 2H, PhCH$_2$O); 5.45 ($m_c$, 2H, OCH$_2$N); 7.14–7.32 (m, 6H, H—C(6), Ph).

The assignment of the signals was carried out with the aid of a $^1$H, $^1$H-COSY spectrum.

$^{13}$C-NMR (50 MHz, $CDCl_3$): 13.39 (CH$_3$—C(5)); 19.63 (C(3')); 24.90 (C(9'); 25.37 (C(5')); 27.39 (C(4')); 27.84 (C(CH$_3$)$_3$); 41.03 (C(6')); 53.36 (C(1')); 57.71 (C(2')); 70.80 (OCH$_2$N); 72.25 (PhCH$_2$O); 89.97 (C(CH$_3$)$_3$); 109.73 (C(5)); 127.55, 128.20 (5C, Ph); 137.17 (C(6)); 138.16 ($C_{ipso}$); 151.19, 152.15 (O$_2$CN, C(2)); 163.30 (C(4)); 170.45 (C(7')).

The assignment of the signals was carried out with the aid of a $^1$H, $^{13}$C-COSY spectrum.

MS (ESI$^+$): 501.7 [M+H], 384.5 [M+H-Boc]. Anal.: calc. for $C_{26}H_{33}N_3O_6$ (483.56): C, 64.58, H, 6.88, N, 8.69; found: C, 64.45, H, 6.91, N, 8.59.

Preparation of 3-[(Benzyloxy)methyl]-1-[(S,S,S)-2-(tert-butoxycarbonyl)amino-4-(carboxymethyl) cyclohexyl]thymine (14a)

1. Procedure 7.81 g (16.2 mmol) of 13c were dissolved in 225 ml of THF in a 500 ml round-bottomed flask, treated with 50 ml of water and cooled to 0° C. by means of an ice bath. 7.33 g (64.8 mmol) of 30% strength hydrogen peroxide followed by 25 ml of an aqueous solution of 1.36 g (32.3 mmol) of LiOH monohydrate were added, after which the solution became turbid. The ice bath was removed and the reaction mixture was stirred for 45 min. The reaction solution was treated with 25 ml of a 1.5M aqueous Na$_2$SO$_3$ solution and 75 ml of satd NaHCO$_3$ solution. Subsequently, the THF was largely removed in vacuo in a rotary evaporator. The solution was poured onto 350 ml of water and adjusted to pH>12 using a little 2N sodium hydroxide solution. The milky suspension was extracted three times with 350 ml of CH$_2$Cl$_2$ each time and the combined org. phases dried using MgSO$_4$. After removing the solvents in vacuo in a rotary evaporator, 2.00 g of impure 13b were obtained, which was recrystallized from 30 ml of THF and 60 ml of cyclohexane. It was thus possible to recover 1.55 g (25%) of 13b (ent-13b: 27%; rac-13b: 30%). The basic, aqueous phase was adjusted carefully to pH 1–2 with half-concentrated hydrochloric acid and extracted three times with 350 ml of AcOEt each time. After drying using Na$_2$SO$_4$, removing the solvents in vacuo in a rotary evaporator, digesting with 50 ml of Et$_2$O, filtering and drying in an oil pump vacuum, 5.09 g (63%) 14a (ent-14a: 60%; rac-14a: 65%) were obtained as a finely crystalline solid of m.p. 89–91° C.

2. Analytical Data

3-[(Benzyloxy)methyl]-1-[(S,S,S)-2-(tert-butoxycarbonyl)amino-4-(carboxymethyl)cyclohexyl] thymine (14a):

M.p.: 89–91° C. (after digestion with Et$_2$O); ent-14a: 90–92° C. rac-14a: 168–170° C. (THF/cyclohexane). TLC: CH$_2$Cl$_2$/MeOH 15:1, $R_f$ 0.37. Spec. rotation: $[α]_{589}^{20}$=–24.0° (c=0.99, MeOH); ent-14a: $[α]_{589}^{20}$=+23.9° (c=1.05, MeOH). UV (CH$_3$CN): $λ_{max}$ 273.2 (10890). IR (KBr): 3373m, 2974m, 2932m, 1706s, 1691s, 1664s, 1647s, 1534m, 1469m, 1452m, 1365m, 1290m, 1255m, 1175m. $^1$H-NMR (300 MHz, d$_6$-DMSO): 0.88–1.30 (m, 2H, H—C (4) H—C(6)); 1.19 (s, 9H, C(CH$_3$)$_3$); 1.66–2.00 (m, 5H, 2H—C(3), H'—C(4), H—C(5), H'—C(6)); 1.80 (s, CH$_3$—C(5')); 2.16 ($m_c$, 2H, CH$_2$COOH); 3.79 ($m_c$, H—C(1)); 4.27 ($m_c$, H—C(2)); 4.58 (s, 2H, PhCH$_2$O); 5.34 (s, 2H, OCH$_2$N); 6.86 (d, J(H—N, H—C(1))=9.6, NH); 7.23–7.37 (m, 5H, Ph); 7.68 (br. s, H—C(6')); 12.09 (br. s, CH$_2$COOH).

The assignment of the signals was carried out with the aid of a $^1$H, $^1$H-COSY spectrum.

$^{13}$C-NMR (50 MHz, CDCl$_3$): 13.09 (CH$_3$—C(5')); 28.11 (C(CH$_3$)$_3$); 30.13 (C(3)); 31.07 (C(4); 33.38 (C(5)); 39.23 (C(6)); 40.18 (CH$_2$COOH); 51.38 (C(1)); 58.19 (C(2)); 70.83 (OCH$_2$N); 72.17 (PhCH$_2$O); 80.05 (C(CH$_3$)$_3$); 110.06 (C(5')); 127.62, 127.69, 128.27 (5C, Ph); 135.46 (C(6')); 138.00 ($C_{ipso}$); 152.72, 155.43 (O$_2$CN, C(2')); 163.20 (C(4')); 176.30 (CH$_2$COOH).

The assignment of the signals was carried out with the aid of a $^1$H, $^{13}$C-COSY spectrum.

MS (ESI$^+$): 519.7 [M+H+H$_2$O]. Anal.: calc. for $C_{26}H_{35}N_3O_7$ (501.58): C, 62.26, H, 7.03, N, 8.38; found: C, 62.00, H, 6.96, N, 8.17.

Preparation of 1-[(S,S,S)-2-(tert-Butoxycarbonyl) amino-4-(carboxymethyl)cyclohexyl]thymine (14b)

1. Procedure 300 mg of Pd—C were suspended in 60 ml of anhydrous THF in a 500 ml three-necked flask and the mixture was saturated with hydrogen for 45 min. Subsequently, a solution of 2.01 g (4.00 mmol) of 14a in 30 ml of THF was added and the reaction mixture was stirred intensively under a hydrogen atmosphere for 90 min (TLC checking; CH$_2$Cl$_2$/MeOH 15:1).

The catalyst was filtered off through Celite and the solvents were removed in vacuo in a rotary evaporator. 1.96 g of a colourless foam were obtained, which was dissolved in 90 ml of anhydrous MeOH and treated with 454 mg (8.40 mmol) of NaOMe. The mixture was stirred overnight at room temp. with exclusion of water. It was treated with 6 ml of satd NH$_4$Cl solution and the solvents were largely removed in vacuo in a rotary evaporator. The residue was poured onto 50 ml of water, the pH of the aqueous phase was adjusted to 1–2 using 2N hydrochloric acid and the aqueous phase was extracted four times with 50 ml of AcOEt each time. After drying using Na$_2$SO$_4$ and removing the solvents in vacuo in a rotary evaporator, the foam obtained was digested with 20 ml of Et$_2$O. After filtration of the precipitate and drying in an oil pump vacuum, 1.43 g (94%) of 14b (ent-14b: 90%; rac-14b: 88%) were obtained as a colourless solid of m.p. 231–233° C. An analytical sample was obtained by crystallization from MeOH/water.

2. Analytical Data

1-[(S,S,S)-2-(tert-Butoxycarbonyl)amino)-4-(carboxymethyl)cyclohexyl]thymine (14b):

M.p.: 235–237° C. (MeOH/H$_2$O); evolution of gas; ent-14b: 234–237° C. rac-14b: 231–233° C. (MeOH/H$_2$O); evolution of gas and decomposition; TLC: CH$_2$Cl$_2$/MeOH 5:1, $R_f$ 0.38. Spec. rotation: $[\alpha]_{589}^{20}$=−21.9° (c=0.57, MeOH); ent-14b: $[\alpha]_{589}^{20}$=+21.2° (c=0.53, MeOH). UV ($H_2O$): $\lambda_{max}$ 272.4 (11450). IR (KBr): 3374s, 3187w, 2978w, 2935w, 1702s, 1648s, 1522s, 1394w, 1366w, 1282s, 1254m, 1170m. $^1$H-NMR (300 MHz, $d_6$-DMSO): 0.85–1.38 (m, 2H, H—C(4) H—C(6)); 1.27 (s, 9H, C(CH$_3$)$_3$); 1.62–2.00 (m, 5H, 2H—C(3), H'—C(4), H—C(5), H'—C(6)); 1.73 (s, CH$_3$—C(5')); 2.15 (m$_c$, 2H, CH$_2$COOH); 3.75 (m$_c$, H—C(1)); 4.19 (m$_c$, H—C(2)); 6.77 (d, J(H—N, H—C(1))=9.6, NH); 7.56 (s, H—C(6')); 11.09 (s, H—N(3')); 12.08 (br. s, CH$_2$COOH).

In the region from 6.00–10.0 ppm a number of small signals can be detected, which disappear on heating of the NMR sample to 80° C.

The assignment of the signals was carried out with the aid of a $^1$H, $^1$H-COSY spectrum.

$^{13}$C-NMR (75.5 MHz, $d_6$-DMSO): 12.03 (CH$_3$—C(5')); 27.90 (C(CH$_3$)$_3$); 29.16 (C(3)); 30.72 (C(4); 32.72 (C(5)); 38.06 (C(6)); 40.30 (CH$_2$COOH); 49.71 (C(1)); 57.05 (C(2)); 77.51 (C(CH$_3$)$_3$); 107.65 (C(5')); 138.32 (C(6')); 151.28, 154.79 (O$_2$CN, C(2')); 163.60 (C(4')); 173.35 (CH$_2$COOH).

The assignment of the signals was carried out with the aid of a $^1$H, $^{13}$C-COSY spectrum.

MS (ESI$^+$): 382.3 [M+H]. Anal.: calc. for $C_{18}H_{27}N_3O_6$ (381.43): C, 56.68, H, 7.13, N, 11.02; found: C, 56.45, H, 7.16, N, 10.80.

Example 2
Synthesis of a Couplable Adenine Unit

Preparation of 9-[(S,S,S)-8-Azabicyclo[3.3.1]nonan-7-on-2-yl]-6N-benzoyladenine (15a)

1. Procedure

A 500 ml two-necked round-bottomed flask was loaded with 180 ml of dry DMF and 2.25 g of a suspension of NaH (60 mmol). 7.18 g of 6-N-benzoyladenine (30 mmol) were added in portions and and [sic] the mixture was fed [sic] until the evolution of gas subsided. After 15 min, 7.95 g of iodolactam 9 (30 mmol) were added and the solution was stirred in the dark for 22 h. The solution was then cooled to 0° C. and neutralized by addition of 1M aqueous HCl (24 ml). The solvent was removed under reduced pressure (0.3 mbar, bath temperature 60° C.). The resulting residue was dissolved in 100 ml of MeOH and preabsorbed on 15 g of silica gel. Chromatography on 7×15 cm silica gel using CH$_2$Cl$_2$/MeOH (12:1) afforded 17 g of a yellow oil, which was recrystallized in 15 ml of MeOH to afford 8.2 g of 15a (22 mmol; 73%) of [sic] a colourless solid which was sufficiently pure for further reactions. An analytical sample was obtained by crystallization from MeOH/Et$_2$O.

2. Analytical Data

M.p.: 269–271° C. (decomposition); TLC: CH$_2$Cl$_2$/MeOH 10:1, $R_f$ 0.28; $[\alpha]_D^{20}$ [sic]: +35.9° (c 1.03, MeOH); UV (MeOH): $l_{max}$ [sic] 280 (20329); IR: 3500–3000s, 2938m, 1685m, 1654s, 1610s, 1542w, 1508m, 1490m, 1458s, 1400m, 1341m, 1286s, 1254s, 1168w, 1098w, 799w, 713m, 643w. $^1$H-NMR (300 MHz, $d_6$-DMSO): 1.53–1.72 (m, 3H); 2.08–2.32 (m, 5H); 2.48–2.58 (m, 1H); 4.27 (br. m, 1H, H—C(1')); 4.63 (br. m, 1H, H—C(2')); 7.52–7.58 (m, 2H, Ph); 7.62–7.68 (m, 1H, Ph); 8.04–8.08 (m, 2H, Ph); 8.14 (d, J(H—N(8'), H(C(1'))=4.3 Hz, H—N(8')); 8.70, 8.75 (2 s, 2H, H—C(2); H—C-(8)); 11.18 (s, 1H, H—NC(6)). $^3$C-NMR (75 MHz, $d_6$-DMSO): 18.89, 24.21, 27.27 (C(3'), C(4'), C(9')); 25.15 (C(5')); 36.95 (C(6')); 47.44 (C(1')); 54.21 (C(2')); 125.32 (C(5)); 128.34, 132.28, 133.34 (Ph); 143.05 (C(8)); 150.17 (C(4)); 151.12 (C(2)); 152.59 (C(6)); 165.49 (Bz-C=O); 171.39 (lactam C=O). MS (ESI$^+$): 377 [M+H] (100%); Microanalysis: calculated for $C_{20}H_{20}N_6O_2$: C, 63.83, H, 5.32, N, 22.34; found: C, 63.90, H, 5.45, N, 22.1.

Preparation of 9-[(S,S,S)-8-Azabicyclo[3.3.1]nonan-7-on-2-yl]adenine (15b)

1. Procedure

A 500 ml round-bottomed flask was loaded with 8.2 g of benzoyl-A lactam 15a (22 mmol) and 250 ml of dry methanol. The suspension was heated until 15a had completely dissolved. A solution of 1.62 g of NaOMe in 5.5 l of MeOH was then added and the mixture was stirred at room temperature for 19 h. The resulting suspension was filtered and the precipitate was washed with Et$_2$O. The filtrate was neutralized by addition of ion-exchange resin (Amberlite IR-120, H$^+$ form). The resin was filtered off and the solvent was removed under reduced pressure. The residue was dissolved in 4 ml of MeOH and precipitated by addition of 30 ml of Et$_2$O. The precipitate was filtered and the combined precipitates were dried in vacuo to afford 5.8 g of 15b (21 mmol, 97%), which was sufficiently pure for further reactions. An analytical sample was obtained by crystallization from MeOH/H$_2$O.

2. Analytical Data

M.p.: 300–302° C. (decomposition); TLC: MeOH, $R_f$ 0.35; $[\alpha]_D^{20}$ [sic]: +42.8° (c 0.40, MeOH); UV (MeOH): $l_{max}$ [sic] 260 (16374); IR: 3367s, 3179s, 3101m, 2926m, 2864w, 1651s, 1600s, 1563m, 1470m, 1337m, 1296m, 1258m, 1229m, 1166w, 1107w, 1005w, 802w, 724w, 668w. $^1$H-NMR (300 MHz, $d_6$-DMSO): 1.48–1.67 (m, 3H); 2.04–2.24 (m, 5H); 2.46–2.54 (m, 1H); 4.20 (br. m, 1H, H—C(1')); 4.46 (br. m, 1H, H—C(2')); 7.26 (s, 2H, NH$_2$); 8.06 (d, J(H—N(8'), H(C(1'))=4.3 Hz, H—N(8')); 8.14, 8.35 (2 s, 2H, H—C(2); H—C-(8)). $^{13}$C-NMR (75 MHz, $d_6$-DMSO): 18.94, 24.15, 27.36 (C(3'), C(4'), C(9')); 25.20 (C(5')); 37.03 (C(6')); 47.47 (C(1')); 53.85 (C(2')); 118.75 (C(5)); 139.18 (C(8)); 149.70 (C(4)); 152.15 (C(2)); 156.03 (C(6)); 178.91 (lactams [sic] C=O). MS (ESI$^+$): 273 [M+H] (100%); Microanalysis: calculated for $C_{13}H_{16}N_6O \times H_2O$: C, 53.78, H, 6.25, N, 28.95; found: C, 53.65, H, 6.24, N, 29.12.

Preparation of 9-[(S,S,S)-8-Azabicyclo[3.3.1]nonan-7-on-2-yl]-6-N-dimethylaminomethylideneadenine (15c)

1. Procedure

A 500 ml round-bottomed flask was loaded with 5.58 g of A lactam 15b (20 mmol), 200 ml of dry DMF and 17.1 ml of dimethylformamide diethyl acetal (100 mmol). The mixture was heated at 80° C. for 3 h. The resulting clear solution was concentrated under reduced pressure (0.4 mbar, 60° C. bath temperature) to afford 6.9 g of crude 15c, which was used without further purification.

2. Analytical Data

TLC (Al$_2$O$_3$): CH$_2$Cl$_2$/MeOH 20:1, $R_f$ 0.75; $^1$H-NMR (300 MHz, CDCl$_3$): 1.58–1.79 (m, 2H); 1.89–1.93 (m, 1H); 2.16–2.28 (m, 2H); 2.38–2.51 (m, 3H); 2.69–2.78 (m, 1H); 3.23, 3.28 (2 s, 6H, CH$_3$); 4.38 (br. m, 1H, H—C(1')); 4.68 (br. m, 1H, H—C(2')); 6.62 (d, J(H—N(8'), H(C(1'))=4.3 Hz, H—N(8')); 8.13, 8.54 (2 s, 2H, H—C(2); H—C-(8)); 8.97 (s, 1H, formamidine H). MS (ESI$^+$): 328 [M+H] (100%).

Preparation of 9-[(S,S,S)-8-N-tert-Butoxycarbonyl-8-azabicyclo[3.3.1]nonan-7-on-2-yl]-6N-dimethylaminomethylideneadenine (15d)

1. Procedure

A 250 ml round-bottomed flask was laded with 6.9 g of crude amidine A lactam 15c (20 mmol) and 100 ml of dry CH$_2$Cl$_2$. 2.8 ml of triethylamine (20 mmol) were added with stirring, followed by 8.7 g of Boc$_2$O (40 mmol) and 2.44 g of DMAP (20 mmol). The solution was stirred at room temperature for 16 h until all the starting material had been consumed. The solvent was removed under reduced pressure and the resulting residue was purified by means of chromatography (7×16 cm silica gel, eluent CH$_2$Cl$_2$/MeOH 20:1) to afford 8.2 g of a yellow solid, which was transferred to a 100 ml round-bottomed flask. 50 ml of Et$_2$O were then added and the mixture was sonicated for 2 h under reflux. After cooling to room temperature, the mixture was filtered and the precipitate was treated with Et$_2$O and sonicated with ultrasound once more. Filtration afforded 6.66 g of 15d (78%) of [sic] a slightly yellowish solid, which was sufficiently pure for further reactions.

2. Analytical Data

TLC: CH$_2$Cl$_2$/MeOH 10:1, R$_f$ 0.66; $^1$H-NMR (300 MHz, CDCl$_3$): 1.54 (s, 9H, tert.-Bu); 1.84–2.36 (m, 7H); 2.44 (d, 1H, J=18.5 Hz); 2.77 (dd, J=7.0, 18.5 Hz, 1H; 3.14, 3.20 (2 s, 6H, formamidine CH$_3$); 4.80 (br. m, 1H, H—C(1')); 5.23 (br. m, 1H, H—C(2')); 8.04, 8.48 (2 s, 2H, H—C(2); H—C-(8)); 8.87 (s, 1H, formamidine H). MS (ESI$^+$): 428 [M+H] (100%).

Preparation of 9-[(S,S,S)-8-N-tert-Butoxycarbonyl-8-azabicyclo[3.3.1]nonan-7-on-2-yl]adenine (15e)

1. Procedure

A 250 ml round-bottomed flask was loaded with 6.64 g of amidine A lactam 15d (15.5 mmol) and 150 ml of dry CH$_2$Cl$_2$. 11.55 g of p-toluenesulphonic acid hydrazide (62.0 mmol) were then added followed by 1.47 g of TsOH (7.75 mmol). The solution was stirred at room temperature for 44 h. After the addition of 150 ml of CH$_2$Cl$_2$, the solution was washed three times with water and adjusted to a pH of >12 by addition of 2M NaOH. The combined wash solutions were extracted with 100 ml of CH$_2$Cl$_2$ and the combined organic phases dried over MgSO$_4$. After filtration, the solvent was removed under reduced pressure and the resulting residue was purified by means of chromatography (5.2×20 cm silica gel, eluent: CHCl$_3$/MeOH 30:1) to afford 4.96 g of 15e (86%), which is sufficiently pure for further reactions. An analytical sample was obtained by crystallization from THF/cyclohexane.

2. Analytical Data

M.p.: 211° C. (evolution of gas) 300–302° C. (decomposition); TLC: CHCl$_3$/MeOH 30:1, R$_f$ 0.23; [α]$_D^{20}$ [sic]: +80.6° (c 1.32, CH$_2$Cl$_2$); UV (MeCN/H$_2$O 1:9): l$_{max}$ [sic] 260 (14136); IR: 3406m, 3328m, 3206m, 2941w, 1756s, 1724s, 1701m, 1668s, 1645s, 1597s, 1570m, 1479m, 1414w, 1304m, 1273s, 1251s, 1228m, 1145s, 1034w, 996w, 853w, 760w. $^1$H-NMR (300 MHz, CDCl$_3$): 1.62 (s, 9H, tert.-Bu); 1.81–1.89 (m, 3H); 2.19–2.37 (m, 4H); 2.54 (d, J=18.5 Hz, 1H; 2.86 (dd, J=7.0, 18.5 Hz, 1H); 4.86 (br. m, 1H, H—C(1')); 5.28 (br. m, 1H, H—C(2')); 5.64 (s, 2H, NH$_2$); 8.06, 8.38 (2 s, 2H, H—C(2); H—C-(8)). $^{13}$C-NMR (75 MHz, d$_6$-DMSO): 19.93, 25.45, 27.23 (C(3'), C(4'), C(9')); 25.97 (C(5')); 28.01 (C(CH$_3$)$_3$)); 40.24 (C(6')); 52.65 (C(1')); 53.68 (C(2')); 84.12 (C(CH$_3$)$_3$)); 119.82 (C(5)); 139.20 (C(8)); 150.59 (C(4)); 152.58 (C(2)); 155.55 (C(6)); 158.46 (Boc-C=O); 171.14 (lactams [sic] C=O). MS (ESI$^+$): 373 [M+H] (100%); Microanalysis: calculated for C$_{18}$H$_{24}$N$_6$O$_3$: C, 58.05, H, 6.50, N 22.57; found: C, 58.13, H, 6.51, N, 22.85.

Preparation of 9-[(S,S,S)-8-N-tert-Butoxycarbonyl-8-azabicyclo[3.3.1]nonan-7-on-2-yl]-6N-p-methoxybenzoyladenine (15f)

1. Procedure

A 100 ml two-necked round-bottomed flask was loaded with 4.96 g of Boc-A lactams [sic] 15e (13.3 mmol) and 60 ml of dry CH$_2$Cl$_2$. 5.35 ml of dry pyridine (66.5 mmol) were then added, followed by 1.59 g of DMAP (1.3 mmol). After cooling to 0° C., 5.4 ml of 4-methoxybenzoyl chloride (39.9 mmol) were added dropwise and the mixture was stirred at 0° C. for 15 min. The ice bath was removed and the reaction mixture was stirred at room temperature for 22 h. The reaction mixture was then again cooled to 0° C. and 35 ml of MeOH were added dropwise. After 30 min at 0° C., 80 ml of a saturated solution of NH$_3$ in MeOH were added dropwise. A white precipitate was formed, which dissolved after complete addition of the solution. After 30 min, the ice bath was removed and the reaction was stirred at room temperature for a further 2 h. The solvent was then removed under reduced pressure and the resulting residue was dissolved in 200 ml of CH$_2$Cl$_2$. The solution was washed successively with 150 ml of saturated NaHCO$_3$ solution and aqueous citric acid solution (20%, 2×100 ml), washed [sic] over MgSO$_4$, filtered and concentrated in vacuo. The resulting residue was purified by means of chromatography (5.2× 18 cm silica gel; eluent: EtOAc/MeOH 40:3) to afford 5.93 g of 15f (88%).

2. Analytical Data

M.p.: 110–112° C. (decomposition); TLC: CH$_2$Cl$_2$/MeOH 40:1, R$_f$ 0.44; [α]$_D^{20}$ [sic]: +58.30 (c 1.32, CH$_2$Cl$_2$); UV (MeOH): l$_{max}$ [sic] 288 (30459); IR: 3600–3050m, 2940m, 1757s, 1707m, 1671m, 1604s, 1577m, 1506s, 1458m, 1402m, 1342m, 1251s, 1168m, 1145s, 1100m, 1024m, 893w, 848m, 794w, 761m, 644w. $^1$H-NMR (300 MHz, CDCl$_3$): 1.63 (s, 9H, tert.-Bu); 1.84–1.91 (m, 3H); 2.24–2.40 (m, 4H); 2.55 (d, J=18.5 Hz, 1H); 2.88 (dd, J=7.0, 18.5 Hz, 1H); 3.92 (s, 3H, OMe); 4.95 (br. m, 1H, H—C (1')); 5.28 (br. m, 1H, H—C(2')); 7.01–7.04 (m, 2H, PMBz-H); 8.01–8.04 (m, 2H, PMBz-H); 8.26, 8.81 (2 s, 2H, H—C(2); H—C-(8)); 8.91 (s, 1H, H—NC(6)). $^{13}$C-NMR (75 MHz, CDCl$_3$): 19.95, 25.55, 27.24 (C(3'), C(4'), C(9')); 25.95 (C(5')); 28.06 (C(CH$_3$)$_3$)); 40.28 (C(6')); 52.61 (C(1')); 53.99 (C(2')); 55.54 (OMe); 84.27 (C(CH$_3$)$_3$)); 114.08 (PMBz); 123.12 (C(5)); 126.24 (PMBz); 130.03 (PMBz); 141.58 (C(8)); 149.87 (C(4)); 152.00 (C(2)); 152.31 (C(6)); 152.54, 163.31, 164.02 (PMBZ, PMBz-C=O, Boc-C=O); 171.14 (lactam C=O). MS (ESI$^+$): 507 [M+H] (100%); Microanalysis: calculated for C$_{26}$H$_{30}$N$_6$O$_5$: C, 61.66, H, 5.93, N, 16.60; found: C, 61.75, H, 6.01, N, 16.69.

Preparation of 9-[(S,S,S)-2-(tert-Butoxycarbonyl)amino-4-(carboxymethyl)cyclohexyl]-6-N-p-methoxybenzoyladenine (16)

1. Procedure

A 500 ml two-necked round-bottomed flask was loaded with 5.25 g of PMBzBoc-A lactam 15f (10.36 mmol) and 200 ml of THF. After cooling to 0° C., a solution of 2.17 g of LiOH×H$_2$O (51.8 mmol) in 50 ml of H$_2$O was added dropwise over a period of 20 min. 30 ml of MeOH were then added, the ice bath was removed and the reaction mixture was stirred at room temperature for 1 h. An ion-exchange resin (Amberlite IR-120, H$^+$ form) was then added until a pH of 7 was reached. The resin was removed by filtration and the solution was concentrated under reduced pressure to a volume of 100 ml. 200 ml of H$_2$O were then added and a pH of 2 was adjusted by addition of 1 M aqueous HCl. The solution was extracted with EtOAc (3×200 ml) and the combined organic extracts were dried over MgSO$_4$, filtered and concentrated in vacuo. The resulting residue was dissolved in 25 ml of hot MeOH. The product was then precipitated by addition of 10 ml of H$_2$O. The precipitate was filtered, washed with H$_2$O and dried over P$_4$O$_{10}$ to afford 1.95 g of 16. It was possible to obtain a further 0.57 g from the mother solution and the wash solutions to afford a total yield of 46%.

2. Analytical Data

M.p.: 238–239° C.; TLC: $CH_2Cl_2$/MeOH 10:1, $R_f$0.39; $[\alpha]_D^{20}$ [sic]: +19.9° (c 0.55, MeOH); UV (MeCN/$H_2O$): $l_{max}$ [sic] 290 (22722); IR: 3368m, 2939w, 1710m, 1683s, 1608s, 1577m, 1528m, 1507m, 1458m, 1306m, 1250s, 1175s, 1030w, 842w, 761w. $^1$H-NMR (300 MHz, $d_6$-DMSO): 1.08 (s, 9H, tert.-Bu); 1.09–1.40 (m, 2H); 1.80–2.35 (m, 7H); 3.86 (s, 3H, OMe); 4.07, 4.36 (2 br. m, 2H, H—C(1') H—C(2')); 6.87 (br. s, 1H, NHBoc); 7.06–7.09 (m, 2H, PMBz-H); 8.00–8.05 (m, 2H, PMBz-H); 8.42, 8.86 (2 s, 2H, H—C(2); H—C-(8)); 10.88 (s, 1H, H—NC(6)). $^{13}$C-NMR (75 MHz, $CDCl_3$): 27.73 (C($CH_3$)$_3$)); 30.35, 30.46, 37.95 (C(3'), C(5'), C(6')); 32.89 (C(4')); 40.32 ($CH_2CO_2H$); 51.30 (C(2')); 55.38 (OMe); 77.45 (C($CH_3$)$_3$)); 113.55 (PMBz); 125.24 (C(5)); 125.63 (PMBz); 131.41 (PMBz); 143.48 (C(8)); 150.03 (C(4)); 150.69 (C(2)); 152.38 (C(6)); 154.53, 162.38, 164.77 (PMBz, PMBz-C=O, Boc-C=O); 173.36 ($CO_2H$). MS (ESI$^+$): 525 [M+H] (100%); Microanalysis: calculated for $C_{26}H_{32}N_6O_6$: C, 59.53, H, 6.15, N, 16.02; found: C, 59.35, H, 6.32, N, 15.89.

Example 3

Synthesis of an Oligomer Having the Sequence ATATA

The polymeric carrier used is a polyoxyethylene (POE)/polystyrene copolymer (Tentagel S HMB, 0.23 mmol/g), which has good swelling properties both in aqueous solution and in organic solvents. The aminoethyl functions of the polymer are derivatized with a hydroxymethylbenzoyl (HMB) linker; the loading with the first A unit is carried out using a 5-fold excess according to the symmetrical anhydride method (addition of 2.5 eq. of DIC and 2.5 eq. of DMAP) in the course of 20 h in DCM.

Stepwise lengthening of the oligomer chain is carried out by means of repetitive cycles which consist of removals of the temporary Boc protective groups and couplings of the Boc-protected monomer units. At the end of the synthesis, the N-terminal Boc protective group is removed using 50% TFA/DCM, the oligomer is cleaved from the HMB linker using 2N HCl/MeOH and purified by HPLC for the further transformation experiments.

The standard coupling cycle is described in the table: the Boc protective group of the amino function is removed using 50% TFA/DCM (30 min), then the resin is washed with DCM and neutralized with 1 M DIEA/DMF and washed with DMF until amine-free. The couplings are each carried out after preactivation of the monomer unit (3 eq.) with HATU (3 eq.) in DMF and with addition of 1M DIEA/DMF (6 eq.) and 2M lutidine/DMF (12 eq.). The coupling times are 3 h at room temperature. After completion of the coupling cycles, unreacted amino functions are capped using acetic anhydride (20 eq.) with addition of pyridine (10 eq.). For monitoring the reaction by means of HPLC, after each coupling step a few resin beads were removed which were treated with 50% TFA/DCM for the removal of the Boc protective group. The respective oligomer was then removed using 2N NaOH/MeOH (15 min, RT), and the removal solution was neutralized using HCl and analysed by RP-HPLC.

Figure 4:
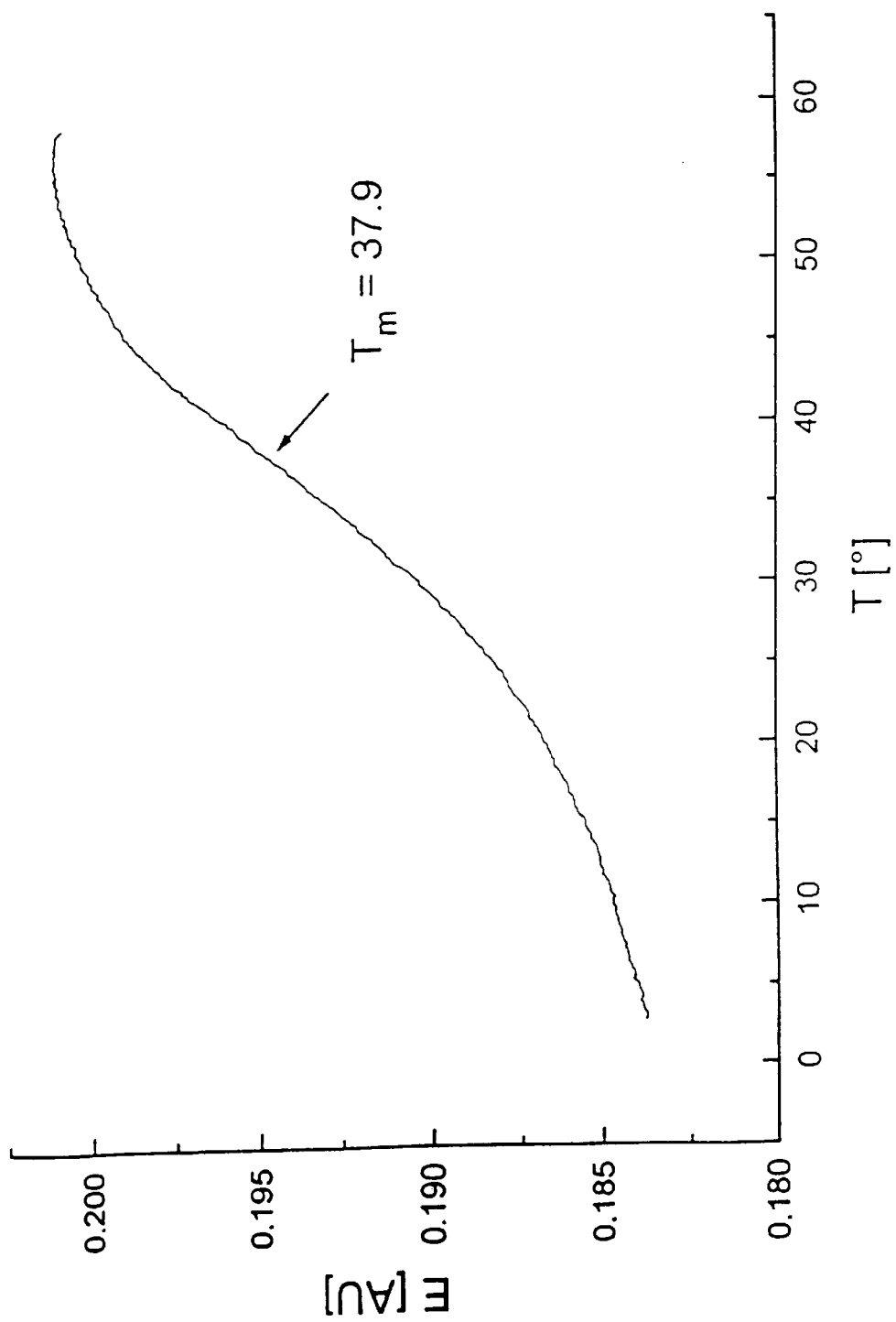

After completion of the synthesis, the removal of the Boc-deprotected oligomers from the HMB resin is carried out, as usual, using 2N NaOH/MeOH (15 min, RT). The removal of the p-methoxybenzoyl protective groups in ($A^{PMBz}$)-containing oligomers is achieved by keeping the removal solution at 55° C. for 2.5 h. Purification is carried out after the neutralization of the removal solution with HCl by RP-HPLC. The isolated HPLC fractions of the synthesis products were checked for their purity using analytical HPLC, clearly characterized using electrospray (ESI) mass spectrometry, and a reversible UV transition curve was recorded (FIG. 4) at 265 nm ($c_{ATATA}$=27.9 $\mu$M in 5 mM Tris/HCl; pH 7.0), by which the suitability as a pairing system is proved.

ATATA:

Mcalc.=1361.0 (M+H) found=1362.0; tR=14.1 min (10 to 40% acetonitrile in 0.1% strength TFA in water in 30 min); Absorption maximum: 263 nm.

Tabular survey of the couplings:

| Operation | Reagent/solvent | Volume | Time |
|---|---|---|---|
| 1. Deblocking | 50% TFA/DCM | 150 $\mu$l | 1 × 5 min |
|  |  |  | 1 × 25 min |
| 2. Washing | DCM | 150 $\mu$l | 5 × (in continuous flow) |
| 3. Neutralization | 1M DIEA/DMF | 75 $\mu$l | 1 × (in continuous flow) |
| 4. Washing | DMF | 150 $\mu$l | 5 × (in continuous flow) |
| 5. Coupling | Unit/HATU/DMF | 80 $\mu$l | 180 min (shaking) |
|  | 1M DIEA/DMF | 12 $\mu$l |  |
|  | 2M lutidine/DMF | 12 $\mu$l |  |
| 6. Washing | DMF | 150 $\mu$l | 3 × (in continuous flow) |
| 7. Analytical method using HPLC: sample removal using 2N NaOH/MeOH (15 min, RT) | | | |
| 8. Capping | $Ac_2O$ | 10 $\mu$l | 20 min (shaking) |
|  | pyridine | 10 $\mu$l |  |
|  | DCM | 100 $\mu$l |  |
| 9. Washing | DCM | 150 $\mu$l | 5 × (in continuous flow) |

Example 4

Reversible Formation of a Homodimeric Peptide

Analogously to Example 3, a sequence AATAT is synthesized on the solid phase, and a Boc-lysine (Fmoc) unit is coupled to this pairing section. The Fmoc group is removed using 40% piperidine in DMF, and the solid phase is washed with DMF and then treated with iodoacetic acid (20 eq.) and DIC (20 eq.) in DMF. After 15 h at RT. the solution is filtered off, and the resin is washed with DMF and treated with the peptide CYSKVG (50 eq.) in DMF. It is left at RT for 15 h, the solution is filtered off and resin is washed with DMF and MeOH. Removal from the resin is carried out using 2M aqueous NaOH with MeOH (1:1) and the removal solution is heated at 55° C. for 2.5 h. After cooling, it is neutralized with 2M hydrochloric acid and the product is isolated using RP-HPLC (10 to 40% acetonitrile in 0.1% strength TFA in water in 30 min). The product fraction (V=3 ml) is freed from the acetonitrile fraction in vacuo and concentrated to 500 $\mu$l of aqueous solution. This solution was desalted by means of a SepPak Plus C18 cartridge (Waters), and adjusted to 1 ml of aqueous solution. The concentration of the oligomer was c=140 $\mu$mol/l (from E=1.004 at 265 nm, measured at 70° C.).

The UV transition curve of a 10 $\mu$molar solution showed that below room temperature the substance was present as a uniform homodimer, while above 40° C. no homodimer can be detected. This equilibrium is reversible, the fraction of homodimer can be adjusted by choice of the temperature and the concentration.

Example 5

Summary of the Thermodynamic Data of Self-complementary CNA Oligomers

| Sequence | Base pairs | Stacks purine-purine | Stacks purine-pyrimidine | $T_m$ (1 μm) [° C.] | $T_m$ (10 μm) [° C.] | $\Delta G$ (298K) [kcal/mol] | $\Delta H$ [kcal/mol] | $\Delta S$ [cal/molK] |
|---|---|---|---|---|---|---|---|---|
| ATATA | 4 | 3 | 0 | 20.9 | 32.3 | −7.52 | −36 | −95 |
| AATAT | 4 | 2 | 2 | 27.4 | 40.5 | −8.47 | −33 | −82 |
| AAATT | 4 | 1 | 4 | 35.0 |  | −9.78 | −49 | −130 |
| TTAAA | 4 | 0 | 2 | 10.0 |  | −6.6 ± 0.5 | −33 | −90 |
| ATATAT | 6 | 3 | 0 | 22.5 |  |  |  |  |
| ATAT | 4 | 2 | 0 |  | ≈−2° | −4.3 | −24 | −65 |

Example 6

Conjugation With a Defined Peptide or a Peptide Library

The conjugation of defined peptides and peptide libraries on CNA was carried out under identical experimental conditions. The conjugation of the CNA Ac-CNA(AATAT)-Lys-OH (1) with the peptide H-Cys-Ser-Lys-Val-Gly-OH (3) is described below.

6.1 Iodoacetylation of (1) on the ε-amino Function of Lysine 1 (0.69 μmol) was dissolved in 800 μl of 0.1 M bicarbonate solution and shaken with 150 equivalents of N-succinimidyl iodoacetate (102 μmol, 28.9 mg) in 400 μl of dimethyl sulphoxide for 2 h with exclusion of light. The product Ac-CNA(AATAT)-Lys(N$^\epsilon$-iodoacetyl)-OH (2) was purified directly by means of preparative RP-HPLC and desalted on an RP-C18 cartridge.

Analytical RP-HPLC: $R_t$=17.93 min.; ESI-MS: $M_r$(calc.)=1699.7, $M_r$(found)=1699.4.

6.2 Conjugation of 2 to H-Cys-Ser-Lys-Val-Gly-OH 3

A solution of 3 (127 nmol, 83 μg, content about 70%) in 30 μl of 0.5 M phosphate buffer, 20 mM EDTA pH 6.0 was added to the solution of 2 (106 nmol) in 20 μl of water/dimethylformamide (1:1) and the mixture was shaken with exclusion of light. After 1 h, the peptide had indeed completely reacted, but the CNA was only reacted to about 50%. By adding the same amount of peptide in buffer again and shaking with exclusion of light for 1 h, 2 was completely reacted. The CNA-peptide conjugate was purified directly by means of RP-HPLC and desalted on an RP-C18 cartridge.

Analytical RP-HPLC: $R_t$=16.93 min.; ESI-MS: $M_r$(calc.)=2227.6, $M_r$(found)=2227.4.

Example 7

Improvement of the Solubility by Phosphation 7.1 General Procedure for the Phosphation of CNA:

7.1.1 Coupling of DMT-protected 4-Hydroxybutyric Acid (Hba) to AATAT-HMB Resin 100 mg of AATAT-HMB resin with a coating of 0.15 mmol/g of resin (0.015 mmol) were neutralized, after the removal of the last Boc protective group, in a 5 ml plastic syringe with a frit using 5 ml of 1M DIPEA solution in DMF and washed 4 times with DMF. 0.15 mmol (61 mg) of DMT-Hba (M=406.48) and 0.15 mmol (57 mg) of HATU (M=380.2) were dissolved in 2 ml of NMP and shaken. After 10 minutes, 0.9 mmol of DIPEA (900 μl of a 1M solution in DMF) was added and shaken. The coupling solution was added to the resin and the syringe with the resin was rotated (about 0.5 rotations/s) around the short syringe axis for 4 h in order to provide for good mixing. The solution was forced out of the syringe and the resin was washed 4 times with 4 ml of DMF and 2 times with 4 ml of DCM.

7.1.2 Detritylation

The resin was detrytylated 5 times with 4 ml of 6% DCA in DCM every 2 minutes and washed 4 times with DCM and 3 times with dry acetonitrile (ACN). The resin was dried over $P_2O_5$ in a desiccator overnight.

7.1.3 Phosphitylation and Oxidation

The resin was swollen under argon using 2 ml of 0.5 M pyridinium hydrochloride in dry ACN. 10 eq. (0.15 mmol, 41 mg) of bis(2-cyanoethyl) N,N-diisopropylaminophosphoramidite (M=271.3) were added and the mixture was rotated for 20 minutes. The resin was washed 4 times with 4 ml of dry ACN and oxidized with 0.5 ml of a 6 M t-BuOOH solution in decane and 1 ml of ACN for 30 minutes. It was then washed 4 times with dry ACN.

7.1.4 Removal of the Cyanoethyl Protective Groups

The resin was treated with 4 ml of a 2 M solution of DBU in pyridine and rotated for 15 h. It was then washed 6 times with ACN.

7.1.5 Removal From the Resin and pMBz Deprotection

Using 2 ml of 2 M NaOH in water, the substance was removed from the resin in the course of 10 minutes. It was washed with a further 2 ml of sodium hydroxide solution and the resulting solution was kept at 55° C. for 3 h. After neutralization with 2 M HCl, the compound was purified on RP-HPLC (eluent water/acetonitrile with 0.1% TFA).

7.1.6

Finally, the substance was desalted on a SEP PAK cartridge (RP) as already described and concentrated to dryness at RT and reduced pressure.

Mass spectrum of $H_2PO_3$-Hba-AATAT ($M_{exact}$=1526.7). Obviously, the molecular ion is singly and doubly charged with Na clusters.

Figure 5:
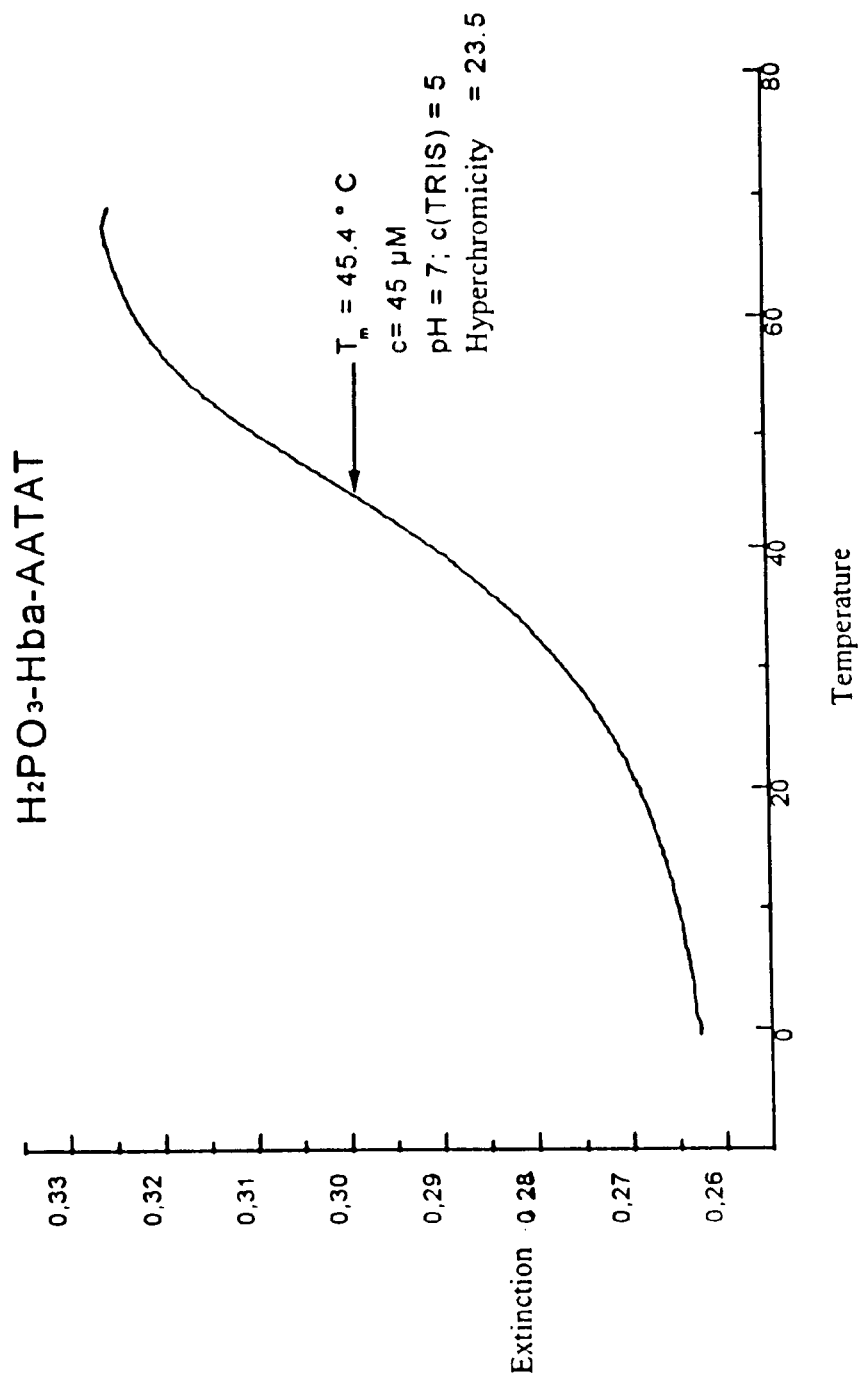

The transition curve is shown in FIG. 5. The $T_m$ value is 45.4° C. The $T_m$ value of AATAT (45 μm) is, by comparison, 49.4° C.

What is claimed is:

1. A compound of the formula (I)

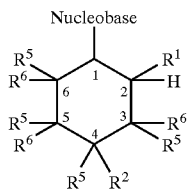
(I)

wherein $R^1$ is equal to $NR^3R^4$, $OR^3$ or $SR^3$, wherein $R^3$ and $R^4$ independently of one another, identically or differently, are H or $C_nH_{2n+1}$, wherein n is equal to an integer from 1–12;

wherein $R^2$ is equal to $C_mH_{2m}$—C(X)—Y where X is equal to =O, =S or =N—H, wherein Y is $OR^3$, $NR^3R^4$ or $SR^3$; or $R^2$ is equal to $C_mH_{2m}$—$CH_2$—X or $C_mH_{2m}$—CH(X)—Y, wherein X is equal to $NR^3R^4$, $OR^3$, or $SR^3$; or $R^2$ is equal to $C_mH_{2m}$—Z—Y' where Z is equal to a $S(=O)_2$ or $P(=O)(O^-)$, wherein Y' is equal to H, $C_nH_{2n+1}$, $OR^3$, $NR^3R^4$ or $SR^3$, and wherein m is an integer from 1–4;

wherein $R^5$, $R^6$ independently of one another are H or $C_nH_{2n+1}$; and wherein nucleobase is selected from the group consisting of 1-thyminyl, 1-uracilyl, 9-adeninyl, 1-cytosinyl, 9-guaninyl, 1-isocytosinyl, 9-isoguaninyl, 9-xanthinyl, and 9-hypoxanthinyl and; wherein each nucleobase is optionally provided with one or more protective groups.

2. The compound according to claim 1, wherein $R^1$ is equal to $NR^3R^4$ or $OR^3$ and $R^2$ is equal to $C_mH_{2m}$—CH(X)—Y where X is equal to $NR^3R^4$, $OR^3$, or SR and Y is equal to $OR^3$, $NR^3R^4$, or $SR^3$.

3. The compound according to claim 1, wherein $R^1$ is equal to $NH_2$ and $R^2$ is equal to $CH_2$—COOH.

4. The compound according to claim 1, wherein the compound is a [2-amino-4-(carboxymethyl)cyclohexyl] nucleobase.

5. The compound according to claim 1, wherein the compound is selected from the group consisting of 1-[2-amino-4-(carboxymethyl)cyclohexyl]thymine, 1-[2-amino-4-(carboxymethyl)cyclohexyl]uracil, 1-[2-amino-4-(carboxymethyl)cyclohexyl]cytosine, 9-[2-amino-4-(carboxymethyl)cyclohexyl]adenine, and 9-[2-amino-4-(carboxymethyl)cyclohexyl]guanine.

6. The compound according to claim 1, wherein the compound is enantiomerically pure.

7. The compound according to claim 1, wherein $R^1$ and/or the nucleobase is provided with protective groups.

8. The compound according to claim 7, wherein the protective groups are selected from the group consisting of tert-butyloxycarbonyl (tBOC), benzyloxymethyl (BOM), 9-fluorenylmethoxycarbonyl (FMOC), ether protective groups, and acetal protective groups.

9. The compound according to claim 1, wherein the nucleobase, $R^1$, and $R^2$ are each substituents of an S-configured chiral center.

10. A process for the preparation of a compound of the following formula (I),

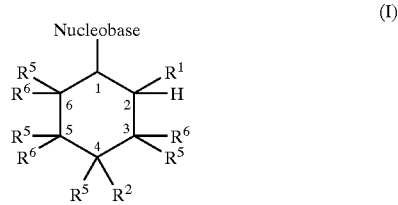
(I)

wherein the variables Nucleobase, $R^1$, $R^2$, $R^3$, $R^4$, $R^5$ and $R^6$ of structure (I) are as defined in claim 2;

the process comprising the steps of:

(a) coupling in the presence of a metal hydride base a protected nucleobase to an iodolactam of the formula (II)

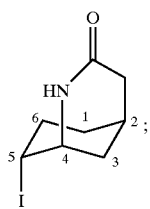
(II)

(b) reacting an alkyloxycarbonyl group with the nitrogen of the lactam ring; and
(c) reacting the product of step (b) with an alkali metal hydroperoxide to open the lactam ring.

11. The process according to claim 10, wherein the iodolactam is present in enantiomerically pure form.

12. The process according to claim 10, wherein the iodolactam is coupled to a protected nucleobase in the presence of an alkali metal hydride.

13. The process according to claim 12, wherein the alkali metal hydride is NaH.

14. The process according to claim 10, wherein the alkyloxycarbonyl group coupled to the nitrogen is a tert-butyloxycarbonyl (t-BOC) group.

15. The process according to claim 10, wherein the alkali metal hydroperoxide is LiOOH.

16. The process of claim 10 further comprising nucleobase-deprotection of the product.

* * * * *